United States Patent
Hamelin et al.

(10) Patent No.: US 9,019,078 B2
(45) Date of Patent: Apr. 28, 2015

(54) SURGICAL OBJECT TRACKING SYSTEM

(75) Inventors: Thomas Hamelin, Cardiff by the Sea, CA (US); Niren Angle, San Diego, CA (US); Milan Makale, San Diego, CA (US); Wolfgang Wrasidlo, La Jolla, CA (US); Sadik C. Esener, Solana Beach, CA (US)

(73) Assignee: The Regents of the University of California, Oakland, CA (US)

(*) Notice: Subject to any disclaimer, the term of this patent is extended or adjusted under 35 U.S.C. 154(b) by 950 days.

(21) Appl. No.: 13/061,897

(22) PCT Filed: Sep. 2, 2009

(86) PCT No.: PCT/US2009/055782
§ 371 (c)(1),
(2), (4) Date: Mar. 2, 2011

(87) PCT Pub. No.: WO2010/028085
PCT Pub. Date: Mar. 11, 2010

(65) Prior Publication Data
US 2011/0163854 A1    Jul. 7, 2011

Related U.S. Application Data

(60) Provisional application No. 61/093,770, filed on Sep. 3, 2008.

(51) Int. Cl.
| | |
|---|---|
| *G06K 7/01* | (2006.01) |
| *G06K 19/02* | (2006.01) |
| *H04Q 5/22* | (2006.01) |
| *A61B 19/00* | (2006.01) |
| *A61B 19/02* | (2006.01) |

(52) U.S. Cl.
CPC ......... *A61B 19/5244* (2013.01); *A61B 19/0287* (2013.01); *A61B 2019/442* (2013.01); *A61B 2019/446* (2013.01); *A61B 2019/4821* (2013.01); *A61B 2019/5265* (2013.01)

(58) Field of Classification Search
CPC ......... G06K 7/01; G06K 19/02; G06K 19/06; B82Y 15/00; B82Y 20/00; H04Q 5/22
USPC ........ 340/10.1–10.5, 568.1; 235/491, 462.01, 235/494; 382/224; 250/458.1, 271, 459.1
See application file for complete search history.

(56) References Cited

U.S. PATENT DOCUMENTS 5,573,529 A * 11/1996 Haak et al. ........................ 606/1
5,608,225 A * 3/1997 Kamimura et al. ........ 250/458.1
(Continued)

OTHER PUBLICATIONS

International Search Report for Priority Application PCT/US2009/055782 dated Mar. 31, 2010.
(Continued)

*Primary Examiner* — Nam V Nguyen
(74) *Attorney, Agent, or Firm* — Mark D. Wieczorek; Mayer & Williams, PC

(57) ABSTRACT

A method and apparatus for identifying and tracking surgical objects is disclosed. More specifically, a method and apparatus for identifying and tracking surgical objects such as needles, scalpels, blades, sponges and instruments in a medical industry using an identifier encoded on a fluorescent paint attached to the surgical object combined with detectors and software capable of retrieving the identifying information on the identifier.

6 Claims, 6 Drawing Sheets

(56) References Cited

U.S. PATENT DOCUMENTS

| | | | |
|---|---|---|---|
| 6,234,537 B1 * | 5/2001 | Gutmann et al. | 283/86 |
| 6,605,049 B1 * | 8/2003 | Wagner et al. | 600/585 |
| 6,777,623 B2 | 8/2004 | Ballard | |
| 6,832,783 B2 * | 12/2004 | Lawandy | 283/85 |
| 7,227,469 B2 | 6/2007 | Varner et al. | |
| 7,362,228 B2 | 4/2008 | Nycz et al. | |
| 7,619,819 B2 * | 11/2009 | Moon et al. | 359/569 |
| 7,938,331 B2 * | 5/2011 | Brock et al. | 235/462.01 |
| 8,081,792 B2 * | 12/2011 | Moon et al. | 382/100 |
| 8,137,210 B2 * | 3/2012 | Gobush | 473/353 |
| 2002/0021003 A1 | 2/2002 | McGrew | |
| 2002/0029032 A1 | 3/2002 | Arkin | |
| 2008/0042106 A1 * | 2/2008 | Champ et al. | 252/408.1 |
| 2008/0280342 A1 * | 11/2008 | Hiyama et al. | 435/174 |
| 2009/0317002 A1 * | 12/2009 | Dein | 382/224 |

OTHER PUBLICATIONS

Written Opinion of the International Searching Authority for Priority Application PCT/US2009/055782 dated Mar. 31, 2010.

* cited by examiner

SURGICAL OBJECT TRACKING SYSTEM

RELATED APPLICATIONS

This application claims the benefit of priority from and incorporates by reference herein, U.S. Provisional Application No. 61/093,770, filed Sep. 3, 2008.

BACKGROUND OF THE INVENTION

The present invention generally relates to an apparatus and a method for identifying and tracking disposable objects and surgical instruments in surgical operating rooms. More specifically, the present invention relates to a system and method to identify and count surgical objects such as needles, scalpels, blades have long been used in the medical profession to help and assist doctors and nurses with their medical needs. In some instances, these types of surgical objects have been left unaccounted for and to the detriment of those within an operating theatre, have caused serious injury. Some current methods of manually counting and tracking these potentially dangerous items include utilizing the nurses within the hospitals.

Moreover, other objects such as sponges may be heavily used during surgery and some of these can easily be left behind unaccounted for. Some conventional techniques for tracking sponges have used radio frequency identification (RFID).

A wide array of surgical instruments may be employed during a surgery and these can be left behind in the patient, creating a serious health hazard. One other known technique uses a bar code system on instruments but this may impose tedium as the barcode can sometimes only be read by the detection system if the labeled object is held at a certain angle, and effective detection of the barcode may require more than one pass.

Hence, it can be seen that a need exists for a system and method of for automated tracking of surgical objects used in a surgical theatre.

SUMMARY OF THE INVENTION

In one aspect of the present invention a system for identifying and tracking a surgical object comprises a tag identifier including object information encoded on a fluorescent paint coating attached to a surgical object; a detector disposed to receive a reflection of the fluorescent paint from the tag identifier; and a receiver in communication with the detector receiving a signal transmitted by the detector wherein the signal is generated by the reflection of the tag identifier.

In another aspect of the present invention a tag identifier comprises one or more quantum dots arranged to define a spectral signature; and a layer coating comprising the one or more quantum dots, wherein the layer coating is attached to an object.

In still yet another aspect of the present invention a method of tracking surgical objects comprises steps including passing a surgical object including a fluorescent tag identifier by a detector; logging a first signal generated by the detector detecting the fluorescent tag identifier; generating an event marking an introduction of the surgical object into an operation area based on the logged signal; passing the surgical object after use back through the detector; logging a second signal generated by the detector detecting the fluorescent tag identifier of the surgical object; and determining that the surgical object is accounted for based on the logged second signal.

These and other features, aspects and advantages of the present invention will become better understood with reference to the following drawings, description and claims.

DETAILED DESCRIPTION OF THE INVENTION

The following detailed description is one of the best currently contemplated modes of carrying out the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Figure 1A:
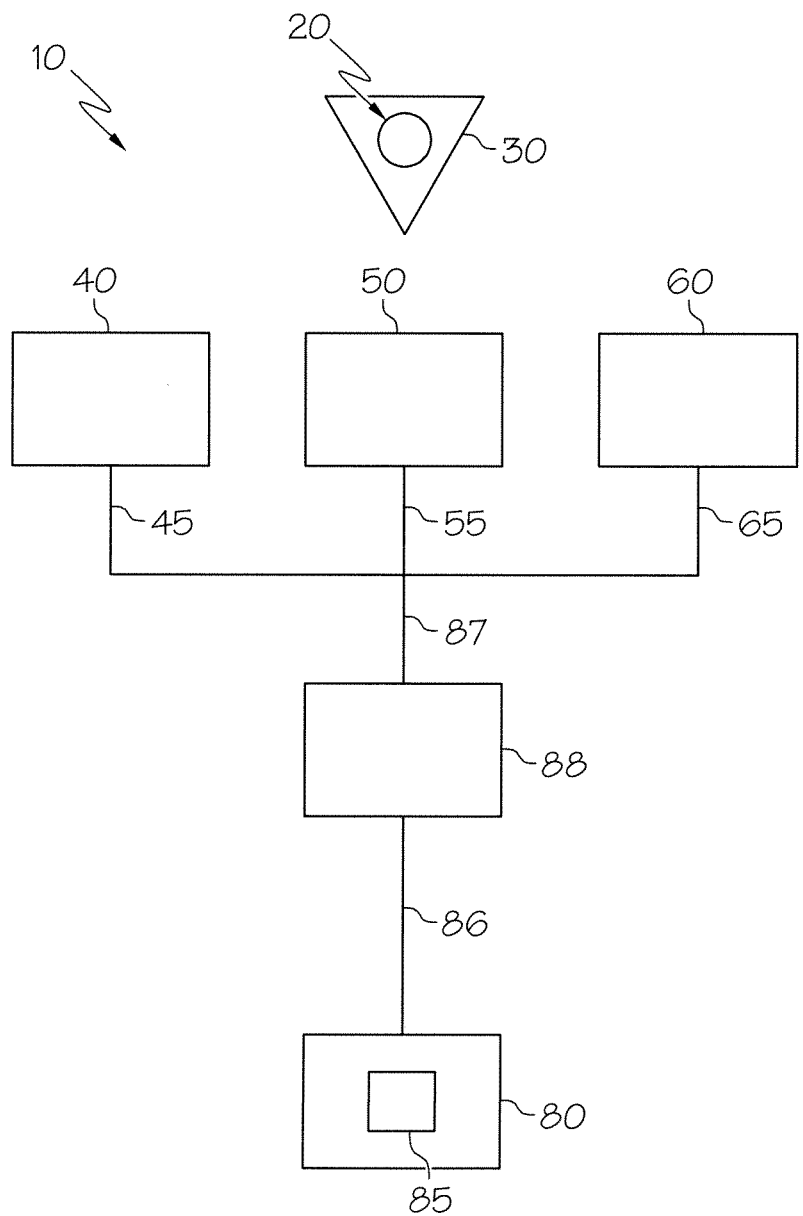
FIG. 1A depicts a tracking system according to an exemplary embodiment of the present invention.

Referring to FIG. 1A, a system 10 in accordance with one exemplary embodiment may generally include an identifier tag 20, a detector 50, an amplifier-digitizer 88, and a computer 80. The system 10 may further include a light source 40, and a motion detector 60. A surgical object 30 may be a sharp instrument such as a scalpel that is coated with an identifier tag 20. Other exemplary surgical objects 30 usable according to exemplary embodiments of the present invention may include a needle, a blade, or any other sharp object ("sharps"), a blunt surgical instrument, or a surgical sponge. Tag identifier 20 may be used for identifying the type of object to which it is attached and counting the number of same type objects having passed by or through the detector 50. In addition to the classification information, other information could also be embedded in the tag identifier such as an object length, an object gauge, a batch number, an instrument type, or any other information that could be of interest in identifying the surgical object 30.

Figure 1B:
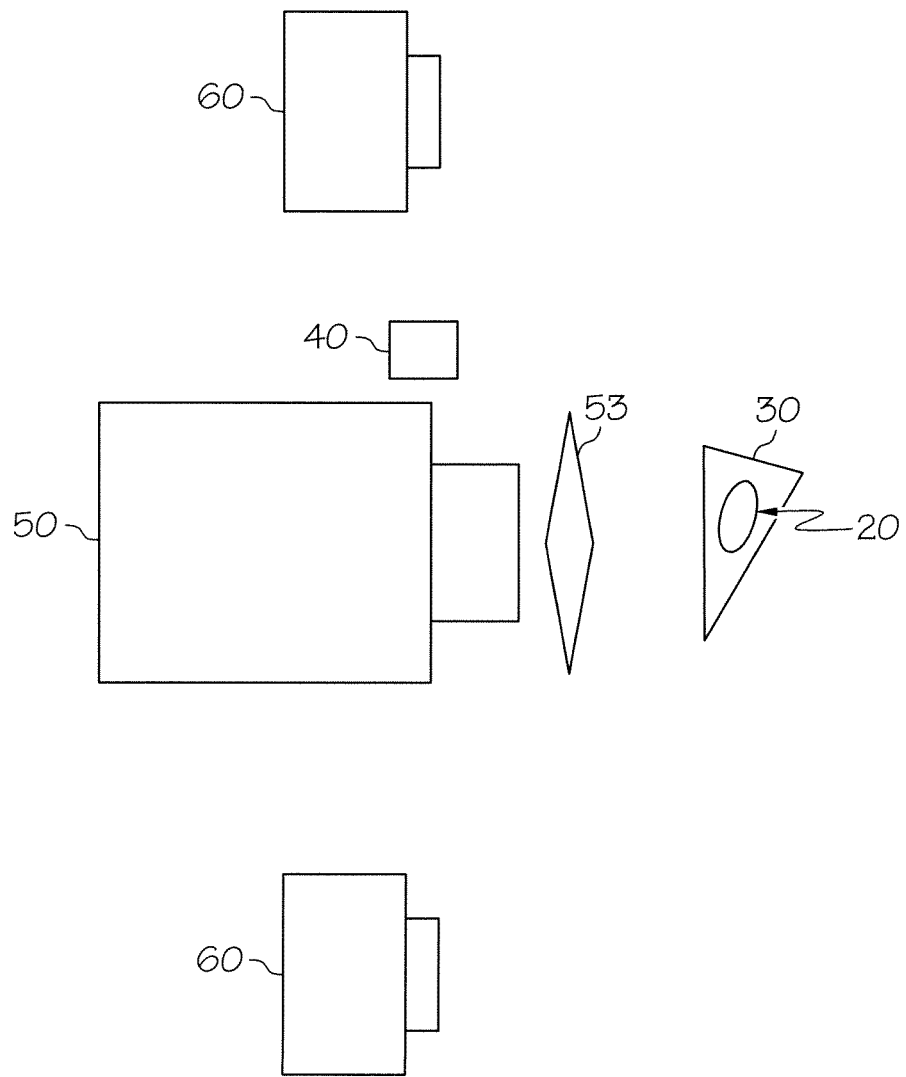
FIGS. 1B and 1C show a top view and a front view respectively of an exemplary setup according to the tracking system shown in FIG. 1A.
Figure 1C:
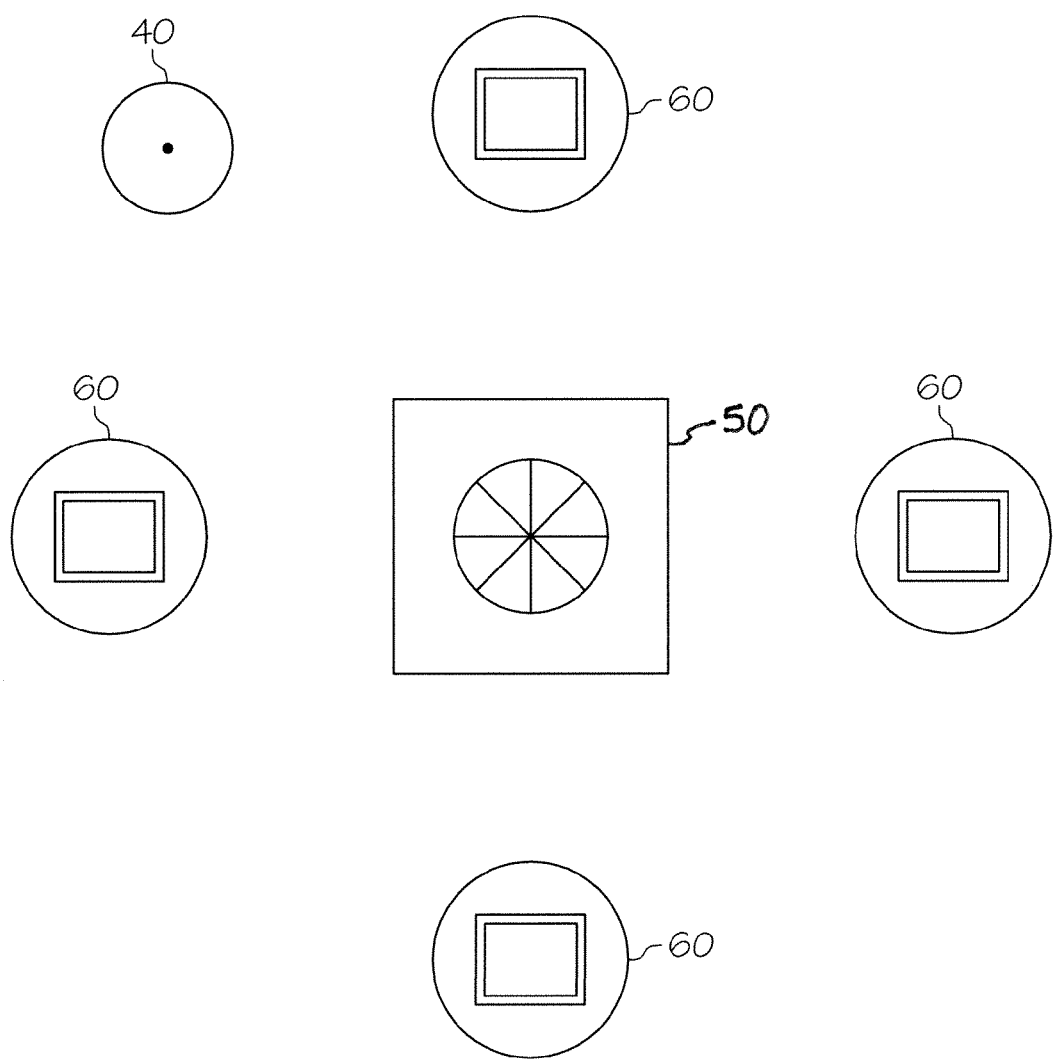

Referring to FIGS. 1B and 1C, an exemplary set up of the elements illustrated in FIG. 1A are shown with the exception of the amplifier-digitizer 88, and the computer 80. As depicted in one exemplary embodiment in FIGS. 1B and 1C, the detector 50 may be a CCD camera. The light source 40 may be positioned near or attached to the detector 50. The detector 50 may be surrounded by one or more motion detectors 60. In one exemplary embodiment, a bandpass filter 53 may be disposed in front of the detector 50 for filtering out unwanted low or high wavelength emissions being detected by the detector 50.

Figure 3:
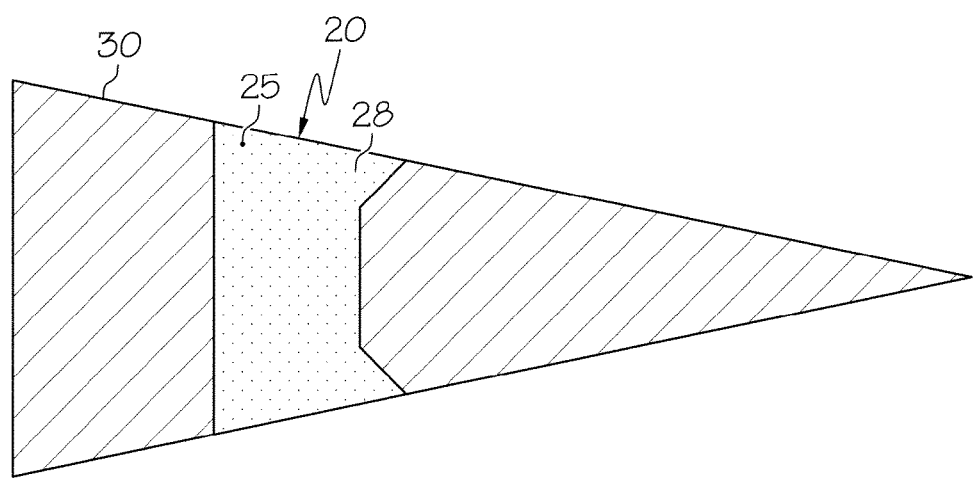
FIG. 3 is a front view of a surgical object including an identifier in accordance with another exemplary embodiment of the present invention.
Figure 5:
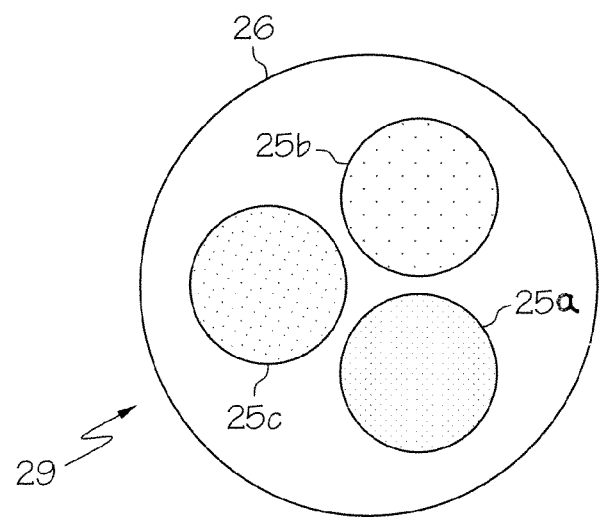
FIG. 5 is a magnified top view of a bead and quantum dots according to another exemplary embodiment of the present invention.
Figure 6:
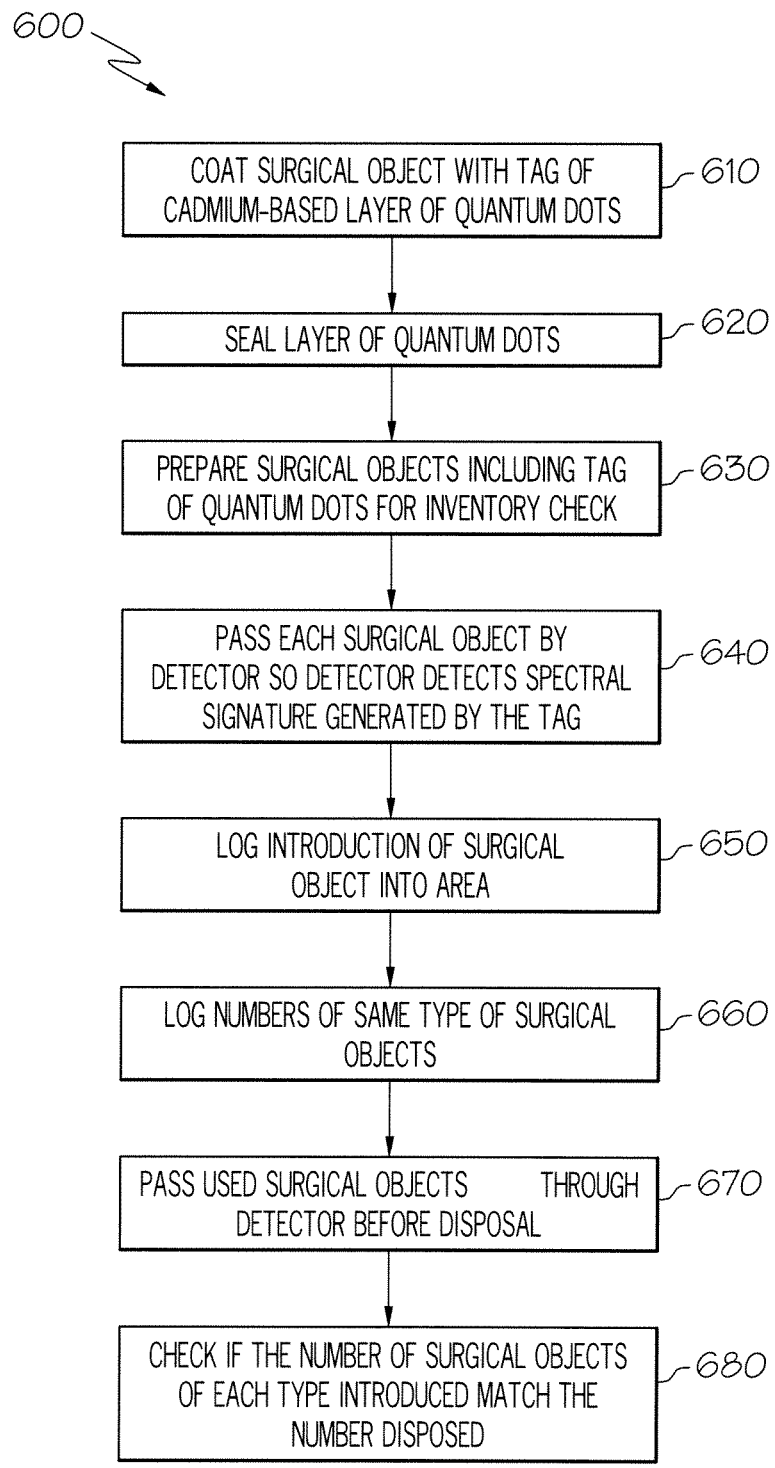
FIG. 6 is a series of steps illustrating a method in accordance with another exemplary embodiment of the present invention.

Referring to FIGS. 3 and 5, the identifier tag 20 may for example, comprise a fluorescent quantum dot deposit of cadmium based quantum dots 25 or organic quantum dots 25. The identifier tag 20 may contain identifying information regarding the surgical object 30. In one exemplary embodiment, the quantum dots may be arranged next to each other in a non-linear formation.

One example of materials used in constructing the tag identifier 20 may be quantum dots 25 made from small, colloidal fluorescent nanocrystals. The quantum dots 25 may be assembled into combinations and adhered to quantum beads 26. A quantum dot 25 may represent one of multiple types as depicted where quantum bead 26 includes quantum dots 25a, 25b, and 25c that may work in combination to provide, for example, at least 400 different specific spectra in the form of a spectral signature 29. The quantum dots 25 can be mixed into liquid solutions and blended with polymer coating materials such as adhesives to be applied as a mechanically resilient coating layer 28 on solid surfaces of surgical objects 30 such as sharps or used in coating formulations on fibrous materials such as in surgical sponges. The coated surgical objects 30 can then be used for fluorescent tagging by optical methods. Some exemplary materials used for producing the quantum dots 25 may include cadmium selenide, cadmium sulfide, indium arsenite, indium phospites of the inorganic type and some quantum dots 25 may be based on organic fluorescent dyes. One exemplary advantage of the quantum dots 25 in accordance with the present invention over other traditional fluorescence organic dyes is their high quantum yield. Thus a very small amount of material may be used to obtain a strong spectral signature 29 signal. For example, the quantum dots 25 may vary in size from 5-100 nm and an exemplary quantum bead 26 may measure up to 1 uM.

Each type of quantum dot (25a, 25b, and 25c) can be produced to obtain a specific signal depending on the frequency of detection desired for an application.

When used in various combinations, quantum dots 25 can be formed into the quantum beads 26, which can be formulated to produce a specific spectral signature 29 identifying a particular surgical object 30 and differentiating the spectral signature 29 from other types. Thus formulation of these quantum beads 26 can be used to tag a specific surgical object 30 and properly identify it.

One exemplary manner of producing coatings may produce both inorganic and organic quantum dots 25 by first dissolving dots in an organic solvent such as toluene, decane, acetone, ethyl acetate or ethylalcohol and then blending these solutions with various resins such as polycyanoacrylates, polymethylmethacrylate, polyurethane or epoxy resins to produce paints which upon solvent evaporation and/or curing yield abrasion resistant coatings on metal objects such as sharps and sponge materials.

Alternatively the quantum dots 25 can be formulated into aqueous dispersions using surfactants and blended with various polymers to obtain latex paints, for coating with surgical objects.

The preparation of coating layer 28 of the tag identifier 20 applied to surgical objects 30 such as sharps, may be radiation resistant, but not resistant to autoclaving as the sharps are not reused; these criteria may be satisfied for example, by using a cadmium based coating. The levels of cadmium can be well below toxic levels. The cadmium-based quantum dots 25 may be extremely fluorescent so they can be applied in minute quantities. The coating layer 28 of the tag identifier 20 may be designed so that it will not rub off the surgical object 30.

Figure 4:
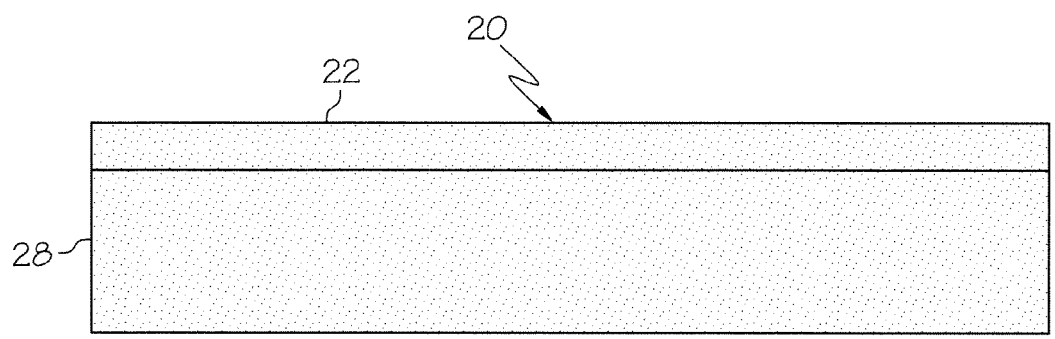
FIG. 4 is a magnified cross-sectional side view of an identifier field shown in FIG. 1.

In one exemplary embodiment, referring specifically to FIG. 4, the coating layer 28 may be covered by an additional, optically transparent sealant 22. The tag identifier 20 may be covered with a thin layer, for example 1 um to 100 um thick of resistant, inert material to prevent interaction with bodily fluids. This inert material serves to protect the tag identifier 20 as well as the doctors and patients who utilize various surgical objects.

Figure 2:
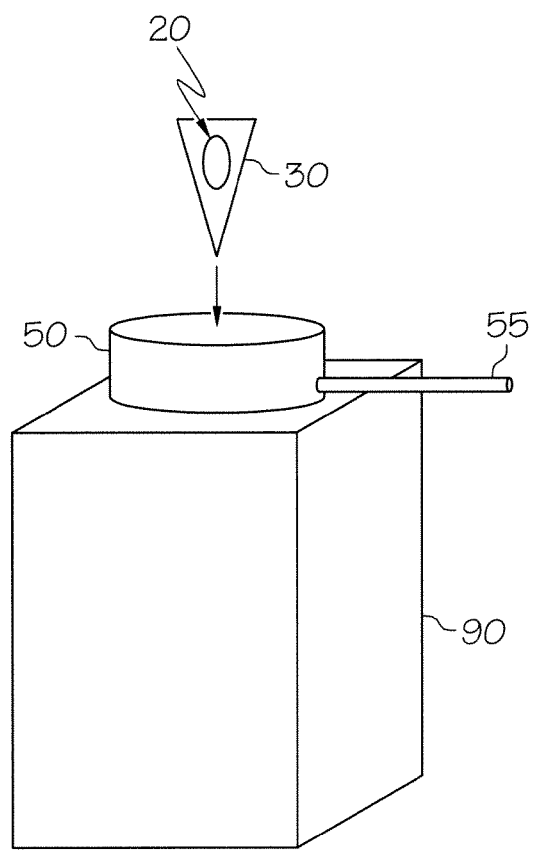
FIG. 2 depicts a surgical object being tracked and disposed of in accordance with the exemplary embodiment of the present invention shown in FIG. 1.

Referring back to FIGS. 1A and 2, detector 50 may be an optical detector such as a CCD camera or a substantially cylindrical array of light detectors, which may within nanoseconds, interrogate a tag identifier 20 of a surgical object 30 passing by CCD camera or through the detector array. As surgical objects 30 pass by or through the detector 50, light shined on the tag identifier 20 may be reflected onto and sensed by the detector 50 thus, producing a signal from the reflection of the tag identifier 20. The detector 50 may also include a wireless antenna 55 for transmitting signals wirelessly. In another exemplary embodiment, the detector 50 may also be connected to a motion detector 60 also including a wireless antenna 65. The detector 50 may have an optical filter 53 to remove non-relevant light wavelengths. It will be understood that the detector array 50 may also use other identifying technologies such as infrared technology, laser scanning technology, or any other types of technology that may be capable of detecting the information embedded within the tag identifier 20.

Motion detector 60 may utilize high frequency, short range waves to detect passage of the surgical object 30 in front of the optical detector 50, thereby triggering the detector 50 to acquire spectral information from the tag identifier 20. The motion detector 60 may operate optically or via sound waves. The motion detector 60 may send information either via cable or through a wireless connection using wireless antenna 65.

The computer system 80 may serve as a receiver for receipt of the information detected and transmitted by the detector 50. A computer system 80 may include a display 85 and be connected an amplifier-digitizer 88 including a wireless antenna 87 receiving signals transmitted from the detector array 50 and motion detector 60. The amplifier-digitizer 88 may acquire via wireless antenna 87 from the detector 50, a signal including information identifying the identifier tag 20 passed through the detector 50. The amplifier-digitizer 88 may amplify the optical spectral signature 29 embedded in the surgical object 30 and may then send the information for analysis in the computer 80 which may then be displayed on the display 85.

The computer system 80 may in one exemplary embodiment, be connected by wireless antenna 86 to amplifier-digitizer 88 in order to analyze, count and display the information gathered from the tag identifier 20 of surgical object 30.

It will also be understood that computer software (not shown) to analyze the fluorescent spectra of the tagged surgical objects 30, count them, display the counts on a screen, and save the count data to a spreadsheet file has been developed by the inventors using the Labview® programming language. The programming in this invention may be extended to include other languages such as C, Pascal, assembler and Java.

In one exemplary use, referring to FIGS. 1B, 2, 4 and 6, a surgical object 30 may be tracked both as it is introduced into an operating area and when it is disposed after use into a disposal container 90. A surgical object 30 should include an identifier tag 20 coated with, for example, a cadmium-based layer of quantum dots 25, (Step 610) sealed by an optically transparent sealant (Step 620). The disposal container 90 may be a disposal receiving container that is generally used in the hospital for disposal or holding of surgical objects 30. It will be understood that one or more detectors 50 may be used simultaneously to identify and track surgical objects 30 being introduced and surgical objects 30 that are being disposed. Thus, one detector array 50 used to track which surgical objects are introduced into an operations table area may be freestanding and separate while another detector array 50 may be attached to the disposal container 90 and may allow an operator to track which surgical objects 30 are being disposed of after use. Thus, surgical objects 30 being introduced during a particular procedure should match up with the type and number of surgical objects 30 disposed of in the disposal container 90.

One or more surgical objects 30 may be prepared for the procedure by being organized together for an inventory check (Step 630). Each surgical object 30 containing the tag identifier 20 may be passed through the detector array 50 wherein the detector array 50 may be activated by movement of the surgical object 30 detected by the motion sensor 60 (Step 640). A light source 40, may be shone upon the tag identifier 20 which may cause the quantum dots 25 to emit a spectral signature 29. The spectral signature 29 (FIG. 5) detected by the detector 50 may be transmitted as a signal via the wireless antenna 55 to the amplifier-digitizer 88. The amplifier-digitizer 88 may filter the transmitted signal including the spectral signature 29 and transform the signal into a readable digital format wherein the signal may be transmitted in turn to the computer system 80. The signal including the spectral signature 29 may be digitally logged (Step 650) and counted (Step 660). Similarly, used surgical objects 30 may be passed by the detector array 50 after use and signals generated by their detection may be logged (Step 670). Thus, a check may be performed to see if each surgical object 30 that was introduced is matched by a surgical object 30 disposed (Step 680). This may include matching a number of the same type of surgical objects 30 sharing a common spectral signature 29 at both the introduction and disposal stages.

Although the current exemplary embodiment utilizes a wireless connection, any other sort of connection that may or may not utilize wires could also be used to connect the various components of the current invention without departing from the scope of the present invention.

While exemplary embodiment of the present invention have been described as employing a tag identifier 20 using quantum dots 25, it may be understood that other embodiments may employ tag identifiers using a barcode, a scanner, a modified radio frequency identification tag able to operate in aqueous environments, or any other identifiable object may be used all without departing from the scope of the present invention; so long as it serves the purpose of embedding the information necessary in an identifiable format.

It should be understood, of course, that the foregoing relates to exemplary embodiments of the invention and that modifications may be made without departing form the spirit and scope of the invention as set forth in the following claims.

What is claimed is:

1. A system for identifying and tracking a surgical object comprising:
    a tag identifier including object information encoded on a fluorescent paint coating attached to a surgical object, the fluorescent paint coating being arranged to emit a fluorescent spectral signature associated with the object information, the tag identifier including a quantum bead incorporating at least one quantum dot, the quantum dot blended with a polymer for mechanical resilience, the quantum dot fluorescing when exposed to a source of light;
    a detector disposed to receive the fluorescent spectral signature emitted from the fluorescent paint of the tag identifier; wherein the quantum bead is formulated to produce the fluorescent spectral signature when exposed to the source of light;
    a receiver in communication with the detector receiving a signal transmitted by the detector wherein the signal is generated by the fluorescent spectral signature emitted from the fluorescent paint of the tag identifier; and
    an amplifier-digitizer connected to the receiver wherein the amplifier-digitizer is configured to filter the signal transmitted by the detector and digitize the signal into a readable format.

2. The system of claim 1, wherein the fluorescent paint comprises colloidal fluorescent nanocrystals.

3. The system of claim 1 wherein the detector is an optical detector.

4. The system of claim 1 wherein the receiver is a computer system configured to analyze the signal and determine the object information encoded on the tag identifier.

5. The system of claim 1 further comprising a motion detector disposed adjacent the detector to sense the surgical object passing by the detector.

6. The system of claim 1 wherein the detector is attached to a disposal container and configured to allow the surgical object to pass by the detector and into the disposal container.

\* \* \* \* \*